United States Patent

Kourtakis et al.

[11] Patent Number: 6,103,653
[45] Date of Patent: Aug. 15, 2000

[54] ATTRITION RESISTANT ZEOLITE CATALYSTS FOR PRODUCTION OF METHYLAMINES IN FLUIDIZED BED REACTORS

[75] Inventors: Konstantinos Kourtakis, Hockessin; Horacio Enrique Bergna; George Carl Sonnichsen, both of Wilmington, all of Del.; David Richard Corbin, West Chester, Pa.; Loren D. Brake, Wilmington, Del.

[73] Assignee: E. I. du Pont de Nemours and Company, Wilmington, Del.

[21] Appl. No.: 08/451,697

[22] Filed: May 26, 1995

Related U.S. Application Data

[62] Division of application No. 08/169,933, Jan. 11, 1994, abandoned.

[51] Int. Cl.[7] .................................................... B01J 29/06
[52] U.S. Cl. .................................... 502/64; 502/63; 502/68
[58] Field of Search .................... 502/63, 64, 68

[56] References Cited

U.S. PATENT DOCUMENTS

| | | | |
|---|---|---|---|
| 3,609,103 | 9/1971 | Gladrow et al. | 252/455 Z |
| 3,867,308 | 2/1975 | Elliott, Jr. | 252/455 Z |
| 3,904,738 | 9/1975 | Robson | 423/328 |
| 4,147,613 | 4/1979 | Gladrow | 208/120 |
| 4,151,119 | 4/1979 | Gladrow | 252/455 Z |
| 4,182,693 | 1/1980 | Gladrow | 252/455 Z |
| 4,206,085 | 6/1980 | Lim et al. | 252/455 Z |
| 4,325,845 | 4/1982 | Lim et al. | 252/455 Z |
| 4,615,996 | 10/1986 | Occelli | 502/65 |
| 4,683,334 | 7/1987 | Bergna et al. | 564/474 |
| 4,752,596 | 6/1988 | Bergna et al. | 502/64 |
| 4,806,689 | 2/1989 | Gier et al. | 564/474 |
| 4,814,503 | 3/1989 | Abrams et al. | 564/474 |
| 4,826,793 | 5/1989 | Velten et al. | 502/64 |
| 4,877,514 | 10/1989 | Hettinger et al. | 208/120 |
| 4,987,110 | 1/1991 | Scherzer | 502/68 |
| 5,141,624 | 8/1992 | Liao et al. | 208/52 |
| 5,250,484 | 10/1993 | Beck et al. | 502/71 |

FOREIGN PATENT DOCUMENTS

| | | | |
|---|---|---|---|
| 0 063 712 | 3/1982 | European Pat. Off. | C10G 11/05 |
| 2 196 872 | 11/1988 | United Kingdom | B01J 21/06 |

OTHER PUBLICATIONS

Hawley, *The Condensed Chemical Dictionary*, 10th Ed. p. 777 (1981), (No Month).

*Primary Examiner*—Tom Dunn

[57] ABSTRACT

This invention provides an attrition resistant catalyst composition and method for producing such composition. The catalyst is comprised of an acidic zeolite, rho or chabazite, and a particulate binder, kaolin, bentonite, alpha-alumina, or titania, which can be optionally modified by treatment with a compound containing Si, Al, P or B. This invention further provides a process for producing methylamines, preferably dimethylamine, comprising reacting methanol and/or dimethyl ether and ammonia in the presence of a catalytic amount of an attrition resistant catalyst of the invention.

7 Claims, No Drawings

ATTRITION RESISTANT ZEOLITE CATALYSTS FOR PRODUCTION OF METHYLAMINES IN FLUIDIZED BED REACTORS

CROSS-REFERENCE TO RELATED APPLICATIONS

This application is a divisional application of Ser. No. 08/169,933 filed Jan. 11, 1994, now abandoned.

This invention relates to attrition resistant zeolite catalysts which are particularly useful for the production of methylamines in fluidized bed reactors.

BACKGROUND OF THE INVENTION

Zeolite catalysts, and especially zeolite rho catalysts and their use in fixed bed reactors for conversion of methanol and ammonia to dimethylamine are well known in the art. (U.S. Pat. No. 3,904,738, U.S. Pat. No. 4,683,334, U.S. Pat. No. 4,752,596, U.S. Pat. No. 4,814,503, and U.S. Pat. No. 4,806,689.) The present invention provides an improvement in these catalysts whereby they are blended with one or more microparticulate binders during formation, which renders the catalyst particles attrition resistant and therefore suitable for use in fluidized bed reactor processes. A particularly useful aspect of the invention is the use of these attrition resistant catalysts in fluidized bed reactors for the efficient and cost effective commercial production of methylamine compounds.

Other examples of improved related catalysts are known in the art. Gladrow et al., (U.S. Pat. No. 3,609,103) disclose use of faujasite and a deagglomerated clay such as Georgia kaolin matrix with a silica-alumina cogel to form a cracking catalyst. The use of the clay phase increases the cracking activity, and thus is added as an active component for the cracking chemistry. Elliott (U.S. Pat. No. 3,867,308) discloses a process for preparing hydrocarbon cracking catalysts using a silica sol by first adding mineral acid to adjust pH, and then adding clay and zeolitic components followed by spray drying. These zeolites are typically X or Y zeolites. Increased attrition resistance and activity of the catalyst, compared to the pure H$^+$ form of the zeolite is disclosed. The process and additive are chosen to increase the activity of the catalyst by adding active components to the formulation. Gladrow (U.S. Pat. No. 4,147,613, U.S. Pat. No. 4,151,119 and U.S. Pat. No. 4,182,693) disclose a hydrocarbon conversion process utilizing catalyst comprising major amounts of silica and minor amounts of zirconia and alumina, bulk alumina and aluminosilicate zeolites. (3–16 wt percent zeolite, 50–85 wt percent inorganic oxide gel, mostly consisting of silica and a minor amount of zirconia and alumina, and 15 to 40 wt percent of a porous absorbent, for instance bulk alumina.) The absorbant is in place to absorb heavy metals present in the petroleum crudes, which can deactivate the zeolite. Increased activity/selectivities for these catalysts compared to a more conventional Y zeolite containing kaolin and a silica-alumina hydrogel is claimed. Lim et al. (U.S. Pat. No. 4,206,085) report an improved abrasion resistant zeolite, prepared from a faujasite type zeolite, hydrated alumina and ammonium polysilicate or silica sol and clay to form microspheres. The use of ball clay is present because the clay has pre-cracking activity which is important in the hydrocarbon chemistry.

Lim et al. (U.S. Pat. No. 4,325,845) describe a method for producing zeolite cracking catalysts using sodium silicate, derived from silica gel, in combination with clay to form catalysts of good attrition resistance. The authors eliminate the alumina from the formulation (pseudoboehmite), claiming it is a source of coking, or deactivation of the catalyst and sodium silicate is substituted for the alumina hydrate. The silicate is added to the ball clay and zeolite to form the final catalyst in order to enhance catalytic activity.

Scherzer (U.S. Pat. No. 4,987,110) claims an attrition resistant cracking catalyst using a molecular sieve (zeolite) having cracking activity, a clay such as kaolin, a silica sol and aluminum chlorohydroxide. In contrast to the present catalysts, the clay disclosed by Scherzer would have significant activity in the methylamines chemistry. Velten et al. (WO 89/01362) claim various zeolites (ZSM-5, ultra stable Y) formulates with binders prepared from amorphous silica, alumina and zirconia, particularly those of colloidal dimensions. Binder formulations include colloidal silica, colloidal alumina, colloidal silica and acid dispersed alumina which may be noncolloidal or colloidal, colloidal silica and colloidal zirconia, or mixtures of these ingredients. Applicants have found that colloidal silicas, aluminas and silica/alumina combinations do not give a satisfactorily attrition resistant rho zeolite at 50 weight percent binder or greater.

SUMMARY OF THE INVENTION

The present invention provides an attrition resistant catalyst composition comprising one or more acidic zeolites selected from rho or chabazite; said zeolite being uniformly admixed to a final weight % of about 25 to 75 with one or more particulate binders selected from kaolin, bentonite, alpha-alumina, and titania; wherein said catalyst composition is optionally modified by treatment with one or more compounds containing elements selected from Si, Al, P and B, said treatment comprising depositing at least 0.05% by weight of the compound onto the surface of the catalyst particles.

The present invention further provides a process for producing a methylamine compound, preferably dimethylamine, comprising reacting methanol and/or dimethylether and ammonia, in amounts sufficient to provide a carbon/nitrogen ratio from about 0.2 to about 2.5, and at a temperature from about 220° C. to about 450° C., in the presence of a catalytic amount of an attrition resistant catalyst composition comprising one or more acidic zeolites selected from rho and/or chabazite; said zeolite being uniformly admixed to a weight % of about 25 to 75 with one or more particulate binders selected from kaolin, bentonite, alpha-alumina, and titania; wherein said catalyst composition is optionally modified by treatment with one or more compounds containing elements selected from Si, Al, P and B, said treatment comprising depositing at least 0.05% by weight of the compound onto the surface of the catalyst particles. Preferably, the above process is used to produce dimethylamine in a fluidized bed reactor.

The present invention further provides a process for the production of an attrition resistant catalyst composition comprising one or more acidic zeolites selected from rho and/or chabazite, said zeolite being uniformly admixed with one or more particulate binders selected from kaolin, bentonite, alpha-alumina, and titania; wherein said catalyst composition is optionally modified by treatment with one or more compounds containing elements selected from Si, Al, P and B, said treatment comprising depositing at least 0.05% by weight of the compound onto the catalyst composition, said process comprising the steps of:

(a) blending one or more acidic zeolites selected from rho and/or chabazite with one or more particulate binders selected from kaolin, bentonite, alpha-alumina, and titania, at a ratio of from about 25 to about 75 weight %;

(b) adding the blend to water to yield a slurry of about 20 to about 55 wt percent solids;

(c) spray drying the slurry to form microspherical particles;

(d) calcining the particles at about 500° C. to about 750° C.; and optionally;

(e) screening the calcined particles to produce a catalyst composition having the desired median particle diameter ($d_{50}$).

DETAILED DESCRIPTION

The advantages of fluid bed catalytic processes over fixed bed processes are well recognized in the art. The advantages in fluid bed processes include improvement of temperature control because of better heat transfer and more efficient solids handling. Particularly in the case of zeolite catalysts for methylamines synthesis, it is recognized that precise temperature control is important to maintain the activity of the catalyst and eliminate the formation of hot spots which are known to occur in fixed bed reactors. Additionally, if the catalyst loses activity with time, it can easily be removed and replaced in a fluid bed reactor. A fixed bed reactor, however, requires the reactor system to be shut down for catalyst removal.

The activity, stability and durability of a catalyst in a fluidized bed catalytic process depend on the inherent attrition resistance of the catalyst particle. Most zeolites, as prepared, do not have the correct particle size range for such a reactor. Hence, they must be formed in the correct particle size range. Attrition by abrasion and/or fracture of the particles is a frequent problem in fluidized reactors, which necessitates the addition of a binder to the catalyst particles. Excessive particle attrition in these reactors is caused, for example, by particle-to-particle contact, abrasion with bed walls and bed internals, as well as distributor jet impingement and abrasion in circulation conduits leading to and from the reactor bed. High particle attrition contributes to product contamination, catalyst loss, plugging of down stream equipment, high filtration costs, and unstable fluidization behavior such as channeling, slugging or increased entrainment of reactants. The deleterious effects of fluidized bed operations can be exacerbated by high temperature conditions. Zeolites by themselves cannot be formed in the correct particle size range with sufficient mechanical strength to be attrition resistant.

In addition to mechanical strength, particle shape can also have an impact on attrition. Spheroidal particles with smooth surfaces will have lower attrition losses than particles with irregular shapes and rough edges. By spheroidal we mean to include spherical and nearly spherical particles, so long as there are no irregular or sharp edges that would likely cause attrition during handling or fluidization.

For a fluid bed methylamines process, a catalyst of high attrition resistance as well as sufficient activity/selectivity is necessary. The use of binders to impart attrition resistance however, introduces additional entities which may have their own reactivities resulting in undesirable competing side reactions. For these reasons, prior literature is not directly applicable in any particular catalytic process. Most previous disclosures in this art concern FCC (fluid cracking catalysts). For these systems, however, the binders are chosen for their catalytic activity towards hydrocarbons. Since fluid cracking is also an acid catalyzed reaction, these FCC catalysts will have undesirable activity on the methylamines reactants. This reactivity is deleterious to the overall selectivity of the catalyst since the molecular sieving characteristic is not a feature of these binders.

Thus, in developing the attrition resistant catalysts of the invention for methylamine production in fluidized bed systems, applicants were faced with many obstacles and constraints. Primarily, the goal was to select the appropriate types and amounts of binders to blend with the appropriate zeolites whereby sufficient catalytic activity and attrition resistance of the catalyst particles was attained for use in commercial fluid bed reactors. Constraints included:

1) minimizing reactivity of the binder phase;
2) controlling the selectivity of the zeolite/binder in producing methylamine compounds in the dimethyl form;
3) producing attrition resistant fluidizable material without excessive heating in order to preserve the integrity of the zeolite.

The attrition resistant catalysts of the invention are either comprised of acidic zeolites rho or chabazite. These and other zeolites can be described as aluminosilicates characterized by a three-dimensional framework structure occupied by ions and water molecules. Rho zeolite and chabazite contain a common structural characteristic: pores or channels within the zeolite framework, the largest of which are bounded by 8-membered rings of tetrahedral atoms. This structural characteristic is associated with catalytic selectivity for production of dimethylamine from methanol and ammonia; the catalyst possesses a geometric or shape selectivity which permits the release of dimethylamine and monomethylamine from the zeolite pores, but not trimethylamine.

Zeolite rho is a small-pore synthetic zeolite which can be described by the formula $$(Na,Cs)_{12}Al_{12}Si_{36}O_{96} \cdot 44H_2O.$$

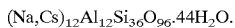

The structure and synthesis of this synthetic zeolite are described by Robson et al., "Synthesis and Crystal Structure of Zeolite Rho—A New Zeolite Related to Linde Type A", Advances in Chemistry Series 121 (American Chemical Society 1973), and Robson, U.S. Pat. No. 3,904,738, incorporated by reference herein. The cation species $Na^+$ and $Cs^+$ present in rho zeolites can be exchanged with $H^+$ or ammonium ions to prepare an acid or ammoniated form ($NH_4$-rho) which is then converted to the acid form by calcination at elevated temperatures (ion exchange of ammonium for $Na^+$ and $Cs^+$ ions may be incomplete in any given experiment, typically leaving 0.5–1.0 Cs per unit cell; the product of this ion exchange is referred to as $NH_4$-rho; similarly, deammoniation of $NH_4$-rho may not result in complete conversion of all $NH_4$ sites to $H^+$ and/or other acid sites).

Chabazite, a mineral zeolite, has a structure consisting of identical, near-spherical "chabazite cages", each composed of two 6-rings at top and bottom, six 8-rings in rhombohedral positions, and six pairs of adjacent 4-rings. Each cage is interconnected to six adjacent units by near-planar, chair-shaped 8-rings. Chabazites can be characterized by the formula:

$$M_a{}^n Al_{12}Si_{24}O_{72} \cdot 40H_2O$$

In this formula, the product of a and n is 12, and M generally refers to Ca, Mg, Na and K. As with rho zeolite, the cations can be exchanged for $H^+$ or by conversion to an ammoniated form which can then be converted to the acid form by calcination at elevated temperatures, generally ranging from 400 to 600° C.

Zeolites rho and chabazite are known to be useful as catalysts for methylamines synthesis in fixed bed reactors.

See U.S. Pat. Nos. 3,904,738, 4,683,334, 4,752,596, 4,814,503 and 4,806,689. The present invention encompasses such known methods of methylamines synthesis in fixed bed reactors, as well as methylamines synthesis in fluidized bed reactors, wherein the catalyst is attrition resistant per the method of this invention, discussed below.

Thus, a process of the present invention comprises reacting methanol and/or dimethylether (DME) and ammonia, in amounts sufficient to provide a carbon/nitrogen (C/N) ratio from about 0.2 to about 2.5, in the presence of a catalytic amount of attrition resistant catalyst composition, at a temperature from about 220° C. to about 450° C. Reaction pressures can be varied from 1–1000 psi (7–7000 kPa) with a methanol/DME space time of 0.01 to 80 hours. The resulting conversion of methanol and/or DME to methylamines is generally in excess of 85% (on a mole basis).

The process variables to be monitored in practicing the process of the present invention include C/N ratio, temperature, pressure, and methanol/DME space time. The latter variable is calculated as the mass of catalyst divided by the mass flow rate of methanol and DME introduced to a process reactor (mass catalyst/mass methanol+DME fed per hour.)

Generally, if process temperatures are too low, low conversion of reactants to dimethylamine and monomethylamine will result. Increases in process temperatures will ordinarily increase catalytic activity, however, if temperatures are excessively high, equilibrium conversions and catalyst deactivation can occur. Preferably, reaction temperatures are maintained between 270° C. and 350° C. more preferably 290° C. to 330° C. with lower temperatures within the ranges essentially preferred in order to minimize catalyst deactivation. At relatively low pressures, products must be refrigerated to condense them for further purification adding cost to the overall process. However, excessively high pressures require costly thick-walled reaction vessels. Preferably, pressures are maintained at 10–500 psi (70–3000 kPa). Short methanol/DME space times result in low conversions and tend to favor the production of monomethylamine. Long methanol space times may result either in inefficient use of catalyst or production of an equilibrium distribution of the products at very high methanol/DME conversions. Generally, methanol/DME space times of 0.01–80 hours are satisfactory, with methanol/DME space times of 0.10–1.5 hours being preferred (corresponding to methanol/DME space velocities of 0.013–100 g methanol+DME/g of catalyst/hour, preferably 0.67–10 g of methanol+DME/g of catalyst/hour).

The molar reactant ratio of methanol and/or dimethylether to ammonia, herein expressed as the C/N ratio (g atoms C/g atoms N), is critical to the process of the present invention. As the C/N ratio is decreased, production of monomethylamine is increased. As the C/N ratio is increased, production of trimethylamine increases. Catalyst deactivation is also greater at high C/N ratios. Accordingly, for best results, C/N ratios should be maintained between 0.2 and 2.5, preferably from 0.5 to 2.2 and most preferably 1 to 2.0 in conducting the process of the present invention.

The efficiency of the process of the invention is measured by overall conversion of methanol and/or DME to methylamines, and by selectivity of dimethylamine production. For example, if methanol is used as the sole reactant, overall conversion is determined by comparison of the amount (in moles) of methanol in the product mixture, which is considered to be unconverted, to the amount in the reactant feed. Thus, overall conversion in percent is given by:

$$100 \frac{(1 - \text{Moles MeOH in Product})}{\text{Moles MeOH in Feed}}$$

Selectivity of methanol to monomethylamine (MMA) in percent, is given by:

$$100 \frac{(\text{Moles MMA})}{\text{Moles MMA} + \text{Moles TMA} + \text{Moles DMA} + \text{Moles DME}}$$

Similarly, selectivity of methanol to trimethylamine (TMA), in percent, is given by:

$$100 \frac{(\text{Moles TMA})}{\text{Moles MMA} + \text{Moles TMA} + \text{Moles DMA} + \text{Moles DME}}$$

Finally, selectivity to dimethylamine (DMA) is calculated by analysis of product composition. Thus, selectivity to DMA, in percent, is provided by the following expression:

$$100 \frac{(\text{Moles DMA})}{\text{Moles MMA} + \text{Moles TMA} + \text{Moles DMA} + \text{Moles DME}}$$

For efficient operation, the catalyst must be selective at high conversion (87–98%) and a C/N ratio of 0.2–2.5, preferably 0.5–2.2, and most preferably 1–2.0.

Comparison of selectivities for different samples should be made at similar conversions since selectivity varies with conversion. At low conversions, MMA production is favored, at very high conversions, the reaction will approach an equilibrium distribution and thus result in increased TMA production.

Because of its high activity and shape selectivity for monomethylamine and dimethylamine, rho zeolite is preferred over chabazite.

The binders of the invention which are admixed with the zeolites may be comprised of one or more of the following metal oxides, most of which are neutral or mildly acidic for use in methylamine synthesis and which have sufficient mechanical properties to confer attrition resistance in microspherical catalysts compositions: alpha-alumina, titania, bentonite and kaolin.

Submicron alpha alumina is most preferred because of its hardness and catalytic inertness. Bentonite is preferred because of its exceptional binding efficiency.

In order to form the catalyst in microspheres, a spray drying process is employed, the first step of which is the formation of an aqueous slurry containing the binder and the zeolite catalyst. In some cases, the pH of this slurry can be important (pH can be adjusted by the addition of an appropriate acid, such as nitric acid). For instance, a range in pH of the composition from <2 to >9 will not significantly change the attrition characteristics of the composition for the bentonite or titania binders. However, for the alpha alumina system, a pH ≦ about 2 (about 1.8) is preferred. In addition, for the alpha alumina systems, it is desirable to hold the slurry, with high speed stirring, for about 1–2 hours prior to use.

The standing particle size of the binders range from 0.2 to 3 micrometers. Alpha alumina is available from various suppliers in the form of powders with a median particle diameter ($d_{50}$) between about 0.2 and 3 micrometers. In the case of Alcoa's A16 SC alpha alumina (Alcoa Industrial Chemicals, Bauxite, AR) a high yield of submicron particles can be obtained by slurrying the powders in water and decanting the fine fraction of particles. Bentonite is an aluminosilicate clay consisting of submicron agglomerates of colloidal particles. It can be obtained from various suppliers, one of which is Southern Clay Products, Gonzales, Tex. as Gellwhite H—NF. $TiO_2$ can be obtained as a submicron powder from Degussa. Much of the $TiO_2$ used in this study is a fumed titania, Degussa's P25 (Degussa, Pigments Division, Ridgefield Park, N.J.). The ultimate particle size of the binder has an influence on the attrition resistance of the zeolite composites. For instance, <0.5 micron alpha alumina binders (with rho zeolite) imparts a lower attrition rate (by about 50%) than 0.5 micrometer alumina. In addition, the crystallite size of the rho zeolite should be micron sized or lower for proper dispersion. Use of a high speed mixer is preferred for proper dispersion of the aqueous slurry used for spray drying.

A preferred catalyst composition is formed using rho zeolite as the catalyst component. In a typical preparation, it was found that the hydrogen form of rho zeolite (calcined) or the ammonium form (uncalcined) could be blended with the appropriate binders by slurrying both components, zeolite and binder with water (water-based solution) to make a 20–50 wt % solids.

The slurry is then spray dried to form the microspherical particles. Spray drying conditions are chosen to produce a particle ranging from 20 to 150 microns. Some experimental parameters, such as slurry concentration, atomization pressure and feed rate can affect the particle size distribution and particle microstructure. These parameters will also vary with the spray dryer configuration and nozzle type used to prepare the material. Applicants used a 4.5 ft i.d. spray dryer fitted with a two fluid nozzle in a counter-current, fountain configuration. Typical conditions include a feed rate of 160 ml/min., inlet temperature of 376° C., and outlet temperatures of 160–170° C.

The spray dried powders are then calcined in air by heating at about 600° C., and maintained at that temperature for 8 hours.

The calcined powder is screened to produce a catalyst in the correct particle size distribution and to minimize particles less than 20 microns in diameter. Typically, a distribution of particles ranging from 20 to about 150 microns in diameter is produced. A median particle diameter ($d_{50}$) of 50 to 70 microns is usually obtained. The median particle diameter ($d_{50}$) is calculated based on median cumulative volume, assuming all particles are spherical. The median cumulative volume is determined from a gaussian distribution based on particle volume.

Additionally, to further enhance selectivity to methylamines, the catalysts of the invention can be modified by treatment with one or more compounds selected from the group consisting of silicon, aluminum, phosphorous, and boron, by depositing at least 0.05 weight percent of the element. Such deposition can be performed at various steps in the catalyst preparation. For a detailed description of such modification methods, see U.S. Pat. Nos. 4,683,334 and 4,752,596.

Attrition measurements are performed using an attrition mill which simulates particle attrition near the gas spargers of a fluidized bed. A catalyst charge is loaded into a column fitted with a single 0.016" perforation. Air flows through the perforation, fluidizes the catalyst bed, and causes attrition. For most measurements, the constant air flow through the mill is calibrated to yield a linear velocity of 760 ft/s through the orifice; this compares to a typical velocity of 150 ft/s in a commercial fuel spargers. The attrition mill measurement accelerates attrition by a factor of roughly thirty. A 24 hour attrition measurement is a reliable indicator of attrition in a commercial reactor. Attrited fines (i.e., those particles lower than 20 micrometers in diameter) are collected in an overhead flask which is fitted with a porous thimble. Flask weight, recorded as a function of time, is used to calculate attrition. The determination of attrition is calculated as an attrition ratio, AR: catalyst attrition divided by the attrition rate of a fluid cracking catalyst standard (FCC). The FCC standard is supplied by Davison Chemical, Baltimore Md. (SMR-5-5209-0293). This catalyst, which contains zeolite Y, is typical of the highly attrition resistant catalysts used in FCC Catalytic Crackers for petroleum refining. As used herein, for a catalyst to be considered attrition resistant, the attrition ratio (AR) should be less than or equal to about 3.

In all cases, in addition to the attrition resistance determined by weighing the fines collected in the flask, the contents of the bed are analyzed by SEM (scanning electron microscopy) as well as for particle size distribution (Coulter Counter or Microtrack techniques) to check that any fines that are produced are properly elutritated (disengaged) from the attrition mills. A catalyst is considered to be attrition resistant only if the weight of fine particles carried over to the flask is acceptably low, and if the contents of the mill do not show any appreciable quantities of fine particles (particles less than 20 microns in diameter).

EXAMPLE 1

50% rho/50% α-alumina

A catalyst composition was formulated using a 50/50 by weight mixture of $NH_4$-rho zeolite to alpha $Al_2O_3$ by the following method.

To 10 gallons of deionized water, 50 g of concentrated HCl acid is added. 6300 g of alpha alumina powder was added (over a period of about 30 minutes) while maintaining the pH (pH=4) with the hydrochloric acid. This slurry was continuously stirred at high speeds for an additional period of 30 minutes. It was then allowed to settle undisturbed for about 4 days. Most of the mother liquor was then decanted off and concentrated by evaporation (boiling, with stirring). This procedure separated the larger alpha alumina particles from the smaller fine particles. These alpha alumina particles (fines) are then submicron in particle size.

In this example, the mother liquor was decanted off and concentrated to about 50.3 wt % solids. 1590 g of this slurry was diluted with 521 g deionized water. 800 grams of the ammonium form of rho zeolite was then added to this slurry (about 55 wt % solids at this point). Concentrated nitric acid was then slowly added, over the course of about 1 hour, to bring the slurry to a stable pH of about 1.9 (about 540 g of nitric acid was added). This was performed while mixing with a stirrer at a speed of about 800 rpm. The slurry was then allowed to sit (with stirring) for another hour. This slurry was not allowed to settle before spray drying, because redispersion would be difficult. The composition of the slurry and the spray dried material contained approximately 50 wt % rho zeolite and 50 wt % of the alpha alumina binder.

This slurry was then poured through a cheesecloth, to filter out any very large clumps of catalyst, and then pumped into a spray dryer. This spray dryer is a 4 ft diameter, 8 ft straight end electrically fired Bowen Dryer. It can operate using a two fluid nozzle in counter current mode or a rotary disk nozzle co-current. In these experiments, a two fluid nozzle was employed. Typical conditions include a feed rate of 160 m/min, an inlet temperature of 376° C. to the dryer and outlet temperatures of 160–170° C.

Spray drying yields were typically 70%. This powder was then calcined in alumina trays to 600° C. for 8 hrs in flowing air. A slow temperature ramp (of about 2–5° C./min) was used. Following this procedure, the catalyst was sieved on +100, −325 mesh screens prior to attrition testing or reactor evaluations.

The catalyst was characterized by a variety of techniques. SEM (scanning electron microscopy) was used to check the formation of the fluidizable microspheres. It was also employed to check the contents of the attrition mills, after an experiment, for any fine particles which may not have elutriated. X-ray diffraction was used to established the integrity of the rho zeolite. Catalysts were evaluated in fixed bed microreactors to check the catalyst activity and selectivity to methylamines as described in Example 8, except where noted. This also applies to examples cited below.

The results of catalyst attrition and activity testing are shown in Table 1 for all examples.

EXAMPLE 2

70% rho zeolite/30% bentonite

A catalyst composition was formulated using a 70/30 by weight mixture of $NH_4$-Rho zeolite to bentonite clay by the same methods employed in Example 1, except for the following differences:

350 g of the ammonium form of rho was slurried with 150 g of bentonite clay (Gellwhite H—NF, Southern Clay Products, Gonzales, Tex.) and 2000 ml deionized water. In this example, the final pH was about 8, and the final wt % solids was 20. This slurry was spray dried and calcined according to the procedure described in Example 1 to produce an attrition resistant catalyst. The approximate final composition is 70% weight rho zeolite/30% weight bentonite clay.

EXAMPLE 3

50% chabazite/50% alpha alumina catalyst

A catalyst was prepared in a similar fashion to that used in Example 1, with the following exceptions:

150 g of chabazite was mixed with 395 g of alumina alumina "fines" slurry (containing 38 wt % of alpha alumina) and 324 g of deionized water (35 wt % solids slurry). The pH of the water and the alumina slurry was adjusted with concentrated nitric acid to a pH of 1.8. The mixture was vigorously stirred for at least 30 minutes prior to spray drying. Other processing steps are similar to those of Example 1, except that the activity testing was conducted at a reaction temperature of 400° C.

EXAMPLE 4

50% rho/50% $TiO_2$ pH=9.5

A catalyst was prepared in a manner similar to Example 1, with the following exceptions:

150 g of rho zeolite was slurried with 150 g of titania (Degussa's P25, Degussa Pigments Division, Ridgefield Park, N.J.) in 1000 g of water. About 2.5 mL of concentrated ammonium hydroxide was added to bring the final pH to 9.5. The slurry was continuously stirred for about 30 minutes prior to spray drying.

EXAMPLE 5

50% rho/50% $TiO_2$ pH=1.8

A catalyst was prepared in a manner similar to Example 1, with the following exceptions:

150 g of rho zeolite was slurried with 150 g of titania (Degussa's P25, Degussa Pigments Division, Ridgefield Park, NJ) in 1000 g of water. Nitric acid was added to bring the final pH to 1.8. The slurry was continuously stirred for about 30 minutes prior to spray drying.

EXAMPLE 6

50% rho/50% kaolin

A catalyst was prepared in manner similar to Example 1, but with the following exceptions:

150 g rho zeolite was mixed with 150 g of kaolin (Engelhard, Edison, N.J.) in 1000 ml of deionized water. The slurry was continuously stirred for 30 minutes prior to spray drying.

EXAMPLE 7

30% rho/70% bentonite

A catalyst was prepared in manner similar to Example 1, but with the following exceptions:

105 g of rho zeolite was slurried with 245 g of bentonite (Gelwhite H—NF, available from Southern Clay Products, Gonzales, Tex.) and 2300 ml of deionized water to make a 13% slurry with pH=8.05. The material was then spray dried.

EXAMPLE 8

TEOS treatment of 50% rho/50% α-alumina

This example demonstrates the utility of tetraethylorthosilicate (TEOS) treatment of 50% rho zeolite/50% α-alumina catalyst to improve methylamines selectivity:

500 g of a 50 wt % rho/50 wt % α-alumina catalyst from Example 1 were slurried with 1500 ml of TEOS. The slurry was then filtered and dried at room temperature, and then calcined for 3 hours at 500° C.

Approximately 2 grams of the catalyst that had been granulated to a 20 to 40 mesh size fraction was placed in a stainless steel U-tube reactor, 0.25 (0.64 cm) in diameter and 18 to 20 in (45.7 to 50.8 cm) in length. The reactor was heated to a reaction temperature of 300° C. in a fluidized sand bath. A 1/1 molar mixture of liquid methanol and ammonia was vaporized and then passed through the reactor into contact with the catalyst at a pressure of 200 psig. The flow rate of the liquid feed was varied from 2 ml/hr to 16 ml/hr. The reactor effluent was continuously analyzed by on-line gas chromatography for dimethyl ether, methanol, water and mono-, di-, and trimethylamine. The methanol conversions and molar selectivities to the amines are listed in Table 1.

Selectivity to a given methylamine is calculated by analysis of product composition as follows:

For example, DMA Selectivity is given by:

$$= 100 * \left[ \frac{\text{Moles DMA}}{\text{Moles MMA} + \text{Moles DMA} + \text{Moles TMA} + \text{Mole DME}} \right]$$

A procedure similar to that described in this example was used to test for methylamines selectivity for the catalysts of other examples.

EXAMPLE 9

Fluidized Bed Testing

A catalyst consisting of TEOS treated 50% rho zeolite/50% alpha alumina (from Example 8) was tested in a fluidized bed reactor used for methylamines synthesis. The catalyst had a particle size distribution ranging from 35 to 235 microns. The fluid bed reactor had an L/D of 16 and L/D of 3 for the disengaging section, and was operated at a temperature of 323° C. and 300 psi. A 1/1 molar mixture of MeOH/$NH_3$ was vaporized at 250° C. and passed at a rate of 497 g/hr through 489 g of the catalyst. The methanol conversion was 89.2%; the feed and product streams were analyzed by on-line gas chromatography. Methylamines selectivity results are shown in Table 1.

COMPARATIVE EXAMPLE A

A 50% zeolite rho with 50% silica (from colloidal source) catalyst shows that silica is detrimental to attrition resistance.

A procedure similar to that described in Example 1 was used. 150 g rho zeolite was mixed with 374.7 g of colloidal silica (40 wt % solution, Ludox® AS-40, available from DuPont, Wilmington, Del., which was acidified with Dowex® HCRW2 resin, available from Dow Chemical Company, Midland, Mich., to a pH=5.3) and 780 ml of water. The slurry was spray dried. This procedure produced a catalyst with attrition ratio, AR>20, which is therefore not attrition resistant.

COMPARATIVE EXAMPLE B

This example demonstrates that the addition of a silica from a colloidal source does not increase the attrition resistance of a rho/bentonite system.

A procedure similar to that described in Example 1 was used. The silica source was polysilicic acid, PSA, which was formed by deionizing sodium silicate with sulfonic acid resin, Dowex® HCRW2 (Dow Chemical Company, Midland, Mich.). For a complete description of the method to prepare aqueous PSA solutions, see U.S. Pat. No. 4,677,084. In this experiment, a 5 wt % $SiO_2$ solution was used. 105 g rho zeolite were mixed with 210 g bentonite (Gellwhite H—NF, Southern Clay Products, Gonzales, Tex.), and 777.4 g of the PSA solution. Additionally, 25 ml $H_3PO_4$ was added to maintain a low pH for PSA stability. This method yield a catalyst have 30% rho zeolite, 60% bentonite and 10% $SiO_2$, which was not attrition resistant, AR>5.

COMPARATIVE EXAMPLE C

A 50% alumina (from colloidal source) binder with 50% rho zeolite to show non-attrition resistance.

A procedure similar to that described in Example 1 was used. 200 g of the ammonium form of rho zeolite, was mixed with 200 g of alumina (1000 g of 20% by weight solution, Nyacol Products, Ashland, Md.) and an additional 142 g of water, resulting in a slurry of about 35% solids by weight. The ph was adjusted with nitric acid to about 2.27. The mixture was slurried for approximately an hour before spray drying.

This procedure produced a catalyst with AR>4, which is therefore not attrition resistant.

COMPARATIVE EXAMPLE D

A 25% silica/25% alumina (from colloidal sources) binder with 50% rho zeolite to show non-attrition resistance.

A procedure similar to that described in Example 1 was used. 200 g of the ammonium form of rho zeolite, was mixed with 150 g of colloidal alumina (750 g of 20% by weight solution, Nyacol Products, Ashland, Md.) and 150 g of silicon oxide (375 g of 40% by weight solution, Ludox® AS-40, available from DuPont, Wilmington, Del.), resulting in a slurry of about 35% solids by weight. The pH was adjusted with nitric acid to about 2.4. The mixture was slurried for approximately an hour before spray drying.

This procedure produced a catalyst with AR>8, which is therefore not attrition resistant.

COMPARATIVE EXAMPLE E

A comparative example with Y zeolite is described below. The catalyst composition is 50 wt % Y zeolite/50 wt % alpha alumina (fines)

A procedure similar to that described in Example 1 was used. 125 g of Y zeolite (ultra stable Y, containing 7% rare earth oxide, Davison Chemical, Baltimore Md.: SMR 6-2558-0491) was added to an acidified slurry of alpha-alumina fines (125 g/0.228= 548 g of slurry. An additional 42 g of deionized water was added to the slurry. The final weight % solids in the slurry was 35%, and the slurry had been acidified, prior to the addition of the zeolite, with nitric acid to a pH of 1.9. The Y zeolite and alpha-alumina fines were held in the slurry for about 15–30 minutes prior to spray drying. This procedure produced a catalyst with AR>4, which is therefore not attrition resistant.

COMPARATIVE EXAMPLE F

A comparative example of 50 wt % Na Mordenite 50 wt % alpha-alumina fines is described below. 369 g of a 38% solids slurry containing alpha-alumina fines (prepared according to the procedure described in Example 1) was used with 302 g of deionized water, acidified with nitric acid to a pH of 1.9. 140 g of Na mordenite was then added to this slurry, which was held for about 30 minutes prior to spray drying. This procedure produced a catalyst with AR>12, which is therefore not attrition resistant. (Note: Mordenite has a channel-like pore structure consisting of twelve-membered rings. The Si/Al ratio in this structure is 5/1, with an ideal unit cell formula $Na_8(AlO_2)_8SiO_2)_{40}.4H_2O$.)

COMPARATIVE EXAMPLE G

A comparative example of 30 wt % $NH_4$-Mordenite 70 wt % bentonite clay is described below.

75 g of the ammonium form of mordenite was slurried with 175 g of bentonite (Englehard Products, Edison, N.J.) and 815 g of deionized $H_2O$. No adjustments to pH were made; the final pH of the slurry was 7.1. This mixture was spray dried and calcined and according to the procedures described in Example 1 and was not attrition resistant.

Scanning electron micrographs of the attrition mill contents, following a 24 hour attrition experiment, showed a majority of particles were below 20 microns. This indicates high attrition rates in the catalyst bed with poor elutriation of the fine particles (below 20 microns in diameter) into the overhead flask in the attrition mill. In addition, the catalyst bed did not fluidize properly after a short time in the attrition mill, which is most likely a result of the improper particle size distribution that results from high attrition rates and poor elutriation of fine particles.

COMPARATIVE EXAMPLE H

A comparative example with Y zeolite (30 wt %) bentonite (70 wt %) is described below.

The ammonium form of Y zeolite (75 g) was used in a slurry of 175 g bentonite (Englehard, Edison, N.J.), 815 g of deionized water (final pH=6.5; 23.5 wt % solids). The material was calcined and treated as in the above examples, and it was not attrition resistant.

Scanning electron micrographs showed that a significant amount of particles were below 20 microns. The catalyst bed did not fluidize properly after a short time in the attrition mill. Additionally, the particle shape was not microspheroidal; the particles were agglomerated into irregular shapes, which also did not fluidize well, making it a poor fluid bed catalyst. (Ammonium exchanged Y zeolite ($NH_4$—Y); Contains 21.4% Si, 9.56% Al, 0.18% Na; available from Linde Division of Union Carbide, N.Y., N.Y.)

TABLE 1

Attrition and Reactor Data

| Ex. | % zeolite | % binder | g recvrd/g std (approximate) std = .05–1.0 g (@ 24 hrs) | % MMA 90% conv. | % DMA 90% conv. | % TMA 90% conv. |
|---|---|---|---|---|---|---|
| 1 | 50% rho | 50% α-$Al_2O_3$ | ~1 | 32 | 59 | 9 |
| 2 | 70% rho | 30% bentonite | ~1 | 33 | 50 | 17 |
| 3 | 50% chabazite | 50% α-$Al_2O_3$ | ~2 | 37 | 49 | 13 |
| 4 | 50% rho pH = 9.41 | 50% $TiO_2$ | ~1 | 32 | 55 | 13 |
| 5 | 50% rho pH = 1.8 | 50% $TiO_2$ | ~1 | 30 | 64 | 6 |
| 6 | 50% rho | 50% kaolin | ~1 | 30 | 58 | 11 |
| 7 | 30% rho | 70% bentonite | ~1–2 | 29 | 60 | 11 |
| 8 | 50% rho (TEOS treated) | 50% α-$Al_2O_3$ | ~1 | 32 | 64 | 4 |
| 9 | 50% rho (TEOS treated; Fluidized Bed) | 50% α-$Al_2O_3$ | ~1 | 32 | 63 | 5 |

What is claimed is:

1. An attrition resistant catalyst composition comprising one or more acidic zeolites selected from the group consisting of rho and chabazite;

said zeolite being uniformly admixed to a ratio of from about 25 to about 75 weight % with one or more particulate binders selected from the group consisting of kaolin, bentonite, alpha-alumina, and titania.

2. The catalyst composition of claim 1 wherein the acidic zeolite is rho.

3. The catalyst composition of claim 2 wherein the rho is $NH_4$-rho.

4. The catalyst composition of claim 1 wherein the particulate binder is alpha-alumina and/or titania.

5. The catalyst composition of claim 1 wherein said catalyst composition is modified by treatment with one or more compounds containing elements selected from Si, Al, P and B, said treatment comprising depositing at least 0.05% by weight of the compound onto the catalyst composition.

6. The catalyst composition of claim 5 wherein said catalyst composition has been modified by treatment with tetraethylorthosilicate.

7. The catalyst composition of claim 5 wherein the acidic zeolite is rho and the binder is alpha-alumina present at a ratio of about 50 weight %; and further wherein said catalyst composition is modified by treatment with tetraethylorthosilicate.

* * * * *